United States Patent
Viste et al.

(10) Patent No.: US 8,675,348 B2
(45) Date of Patent: *Mar. 18, 2014

(54) CAPACITOR ELECTROLYTE

(75) Inventors: Mark E. Viste, Brooklyn Center, MN (US); John D. Norton, New Brighton, MN (US); Joachim Hossick-Schott, Minneapolis, MN (US); Anthony W. Rorvick, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 591 days.

This patent is subject to a terminal disclaimer.

(21) Appl. No.: 12/843,853

(22) Filed: Jul. 26, 2010

(65) Prior Publication Data

US 2010/0289458 A1 Nov. 18, 2010

Related U.S. Application Data

(60) Division of application No. 11/427,919, filed on Jun. 30, 2006, now Pat. No. 7,952,853, which is a continuation-in-part of application No. 10/832,766, filed on Apr. 27, 2004, now Pat. No. 7,081,141, and a continuation-in-part of application No. 10/977,584, filed on Oct. 29, 2004, now abandoned.

(60) Provisional application No. 60/695,670, filed on Jun. 30, 2005.

(51) Int. Cl.
*H01G 9/042* (2006.01)

(52) U.S. Cl.
USPC ........... 361/529; 361/509; 361/523; 361/502; 361/505; 361/508

(58) Field of Classification Search
USPC ......... 361/509, 523, 502, 505, 508, 517, 512, 361/302
See application file for complete search history.

(56) References Cited

U.S. PATENT DOCUMENTS

| 1,960,834 A | 5/1934 | Tyzzer |
| 2,024,210 A | 12/1935 | Edelman |
| 2,739,110 A * | 3/1956 | Ruscetta et al. ............. 205/78 |
| 3,640,854 A | 2/1972 | Klein |
| 3,943,041 A | 3/1976 | Jackson |
| 4,052,273 A | 10/1977 | Aronson et al. |

(Continued)

FOREIGN PATENT DOCUMENTS

| EP | 0989572 A2 | 3/2000 |
| WO | WO 2004/049361 A1 | 6/2004 |

OTHER PUBLICATIONS

Alwitt, "Anodizing," *Electrochemistry Encyclopedia*, Dec. 2002. Retrieved online on Oct. 29, 2010 at <URL:http://electrochem.cwru.edu/encycl/art-a02-anodizing.htm>; 8 pgs.

(Continued)

*Primary Examiner* — Robert J Hoffberg
*Assistant Examiner* — Hung Dang
(74) *Attorney, Agent, or Firm* — Carol F. Barry

(57) ABSTRACT

A capacitor for an implantable medical device is presented. The capacitor includes an anode, a cathode, a separator therebetween, and an electrolyte over the anode, cathode, and separator. The electrolyte includes ingredients comprising acetic acid, ammonium acetate, phosphoric acid, and tetraethylene glycol dimethyl ether. The capacitor has an operating voltage ninety percent or greater of its formation voltage.

25 Claims, 14 Drawing Sheets

(56) References Cited

U.S. PATENT DOCUMENTS

| | | | |
|---|---|---|---|
| 4,473,864 A * | 9/1984 | Van Heusden | 361/327 |
| 5,223,002 A * | 6/1993 | Ross | 29/25.03 |
| 5,716,511 A * | 2/1998 | Melody et al. | 205/324 |
| 5,792,188 A * | 8/1998 | Starkweather et al. | 607/5 |
| 5,837,121 A | 11/1998 | Kinard et al. | |
| 5,861,006 A | 1/1999 | Kroll | |
| 5,882,719 A | 3/1999 | Creasi, Jr. | |
| 5,899,923 A | 5/1999 | Kroll et al. | |
| 5,920,455 A | 7/1999 | Shah et al. | |
| 5,948,216 A | 9/1999 | Cava et al. | |
| 6,006,133 A | 12/1999 | Lessar et al. | |
| 6,042,740 A | 3/2000 | Uehara et al. | |
| 6,096,062 A | 8/2000 | Silvian | |
| 6,183,619 B1 | 2/2001 | Gillman et al. | |
| 6,219,222 B1 * | 4/2001 | Shah et al. | 361/506 |
| 6,231,993 B1 | 5/2001 | Stephenson et al. | |
| 6,235,181 B1 | 5/2001 | Kinard et al. | |
| 6,267,861 B1 | 7/2001 | Kinard et al. | |
| 6,283,985 B1 | 9/2001 | Harguth et al. | |
| 6,377,442 B1 * | 4/2002 | Strange et al. | 361/508 |
| 6,480,371 B1 | 11/2002 | Kinard et al. | |
| 6,551,873 B2 | 4/2003 | Park et al. | |
| 6,587,329 B1 | 7/2003 | Feger | |
| 6,621,686 B1 | 9/2003 | Jenn-Feng et al. | |
| 6,706,059 B2 | 3/2004 | Harguth et al. | |
| 6,761,728 B2 | 7/2004 | Harguth et al. | |
| 6,788,523 B1 | 9/2004 | Hossick-Schott et al. | |
| 6,800,186 B1 | 10/2004 | Forand et al. | |
| 6,802,951 B2 | 10/2004 | Hossick-Schott | |
| 6,815,306 B1 | 11/2004 | Strange et al. | |
| 7,081,141 B2 | 7/2006 | Hossick-Schott et al. | |
| 7,131,988 B2 | 11/2006 | Harguth et al. | |
| 7,171,267 B2 | 1/2007 | Harguth et al. | |
| 7,342,774 B2 | 3/2008 | Hossick-Schott et al. | |
| 7,952,853 B2 * | 5/2011 | Viste et al. | 361/504 |
| 2001/0047190 A1 | 11/2001 | Harguth et al. | |
| 2002/0067589 A1 | 6/2002 | Marshall et al. | |
| 2002/0095186 A1 | 7/2002 | Harguth et al. | |
| 2003/0141193 A1 | 7/2003 | Hossick-Schott | |
| 2004/0028922 A1 | 2/2004 | Reichert et al. | |
| 2004/0098058 A1 | 5/2004 | Harguth et al. | |
| 2004/0134874 A1 | 7/2004 | Hossick-Schott et al. | |
| 2004/0240151 A1 | 12/2004 | Hossick-Schott et al. | |
| 2004/0243183 A1 | 12/2004 | Norton et al. | |
| 2006/0091020 A1 | 5/2006 | Hossick-Schott et al. | |
| 2006/0191796 A1 | 8/2006 | Muffoletto et al. | |
| 2007/0025063 A1 | 2/2007 | Viste et al. | |

OTHER PUBLICATIONS

Evans, "Tantalum Hybrid Button Cell Capacitor," 13th International Seminar on Double Layer Capacitors and Hybrid Energy Storage Devices, Dec. 8-10, 2003, Deerfield Beach, FL; 6 pgs.

Hayward, "Failure Mechanisms in Wet Tantalum Capacitors," *Electrocomponent Science and Technology*, 1976; 2:249-257.

International Search Report for PCT/US2006/026106, Jan. 15, 2007, 5 pgs.

Odynets "Field Crystallization Model in Metal-Oxide-Electrolyte Systems," *Elektrokhimiya*, Dec. 1987; 23(12):1703-1706.

Schau, "Trends in Tantalum Capacitor Development," *Electronic Products*, Mar. 2003, pp. 29-30.

Smyth et al., "The Heat-Treatment of Anodic Oxide Films on Tantalum: I. The Effects on Dielectric Properties," *Journal of the Electrochemical Society*, Dec. 1963; 110(12):1264-1271.

Smyth et al., "The Heat-Treatment of Anodic Oxide Films on Tantalum: IV. Anodization in Phosphoric Acid Solutions," *Journal of the Electrochemical Society*, Feb. 1966; 113(2):100-104.

Torrisi, "Relation of Color to Certain Characteristics of Anodic Tantalum Films," *Journal of the Electrochemical Society*, Apr. 1955; 102(4):176-180.

Zednicek et al., "A Study of Field Crystallization in Tantalum Capacitors and its Effect on DCL and Reliability," Capacitor and Resistor Technology Symposium, Jacksonville, Florida, Mar. 30-Apr. 2, 2009; available on the Internet: <URL:http://ecadigitallibrary.com/pdf/CARTSUSA09/5.3a%20Zednicek-AVX.pdf; 16 pgs.

* cited by examiner

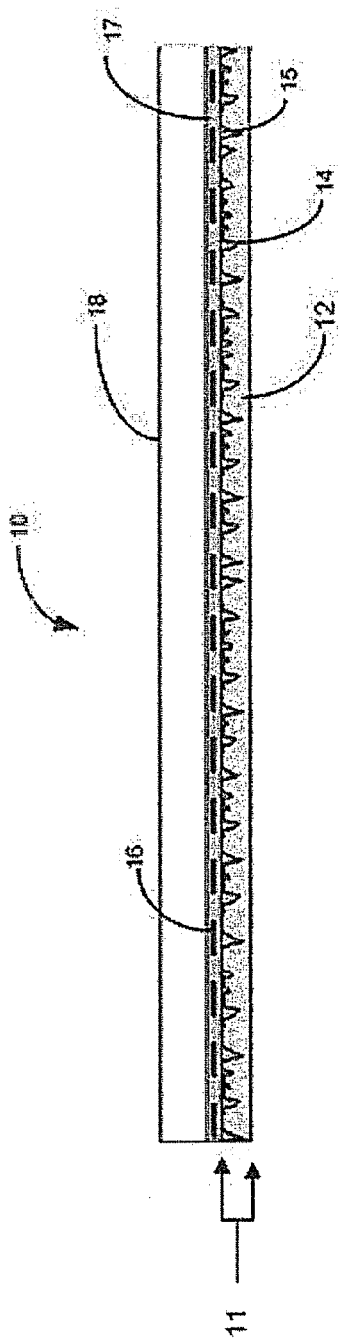
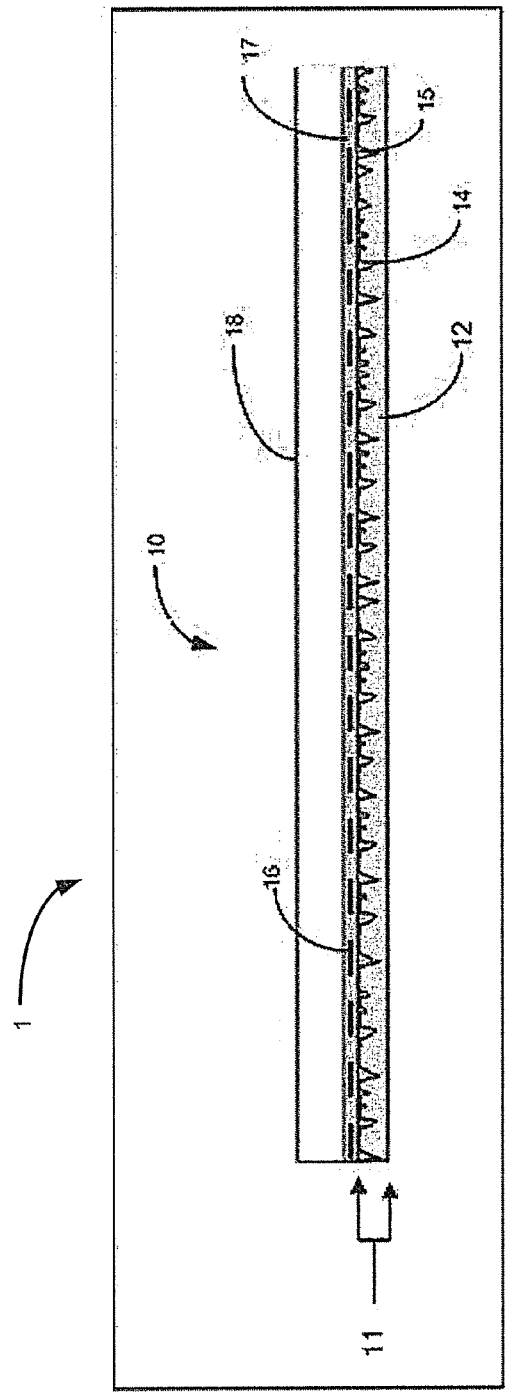

CAPACITOR ELECTROLYTE

CROSS-REFERENCE AND INCORPORATION BY REFERENCE

This patent disclosure is a divisional application of application Ser. No. 11/427,919 filed on Jun. 30, 2006 and entitled "CAPACITOR ELECTROLYTE," which claims the benefit of U.S. provisional patent application Ser. No. 60/695,670 filed on Jun. 30, 2005, entitled, "CAPACITOR ELECTROLYTE," the entire contents of which, including exhibits appended thereto, are incorporated herein by reference. Attention is directed to patent application Ser. No. 10/977,584 filed on Oct. 29, 2004 entitled, "PROCESSES AND SYSTEMS FOR FORMATION OF HIGH VOLTAGE, ANODIC OXIDE ON A VALVE METAL ANODE" published as 2006-0091020-A1 on May 4, 2006 (now abandoned), and patent application Ser. No. 10/832,766 filed on Apr. 27, 2004 entitled, "ELECTROLYTE FOR ELECTROLYTIC CAPACITOR," (now U.S. Pat. No. 7,081,141) the contents of which, including exhibits appended thereto, are incorporated herein by reference in their entireties.

FIELD OF THE INVENTION

The present invention generally relates to implantable medical devices and, more particularly, to capacitors.

BACKGROUND OF THE INVENTION

Implantable medical devices (IMDs) detect and deliver therapy for a variety of medical conditions in patients. Exemplary IMDs include implantable pulse generators (IPGs) or implantable cardioverter-defibrillators (ICDs). ICDs include a circuit that detects abnormal heart rhythms and automatically delivers therapy to restore normal heart function. An ICD circuit includes, inter alia, a battery, a capacitor, and a control module. The battery supplies power to the control module and the capacitor. The control module controls electrical therapy delivered to a patient. For example, the control module signals a switch, coupled to the capacitor, to open or close, which controls whether energy is released by the capacitor. The capacitor delivers bursts of electric current through a lead that extend from the ICD to myocardial tissue of the patient.

Electrolytic capacitors (e.g. tantalum, aluminum etc.) are typically used since these capacitors attain high energy density in a low volume package. Generally, a tantalum electrolytic capacitor's formation voltage is typically three to four times the capacitor's rated voltage. See, John Gill, Basic Tanatlum Capacitor Technology, AVX Journal, p. 3.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
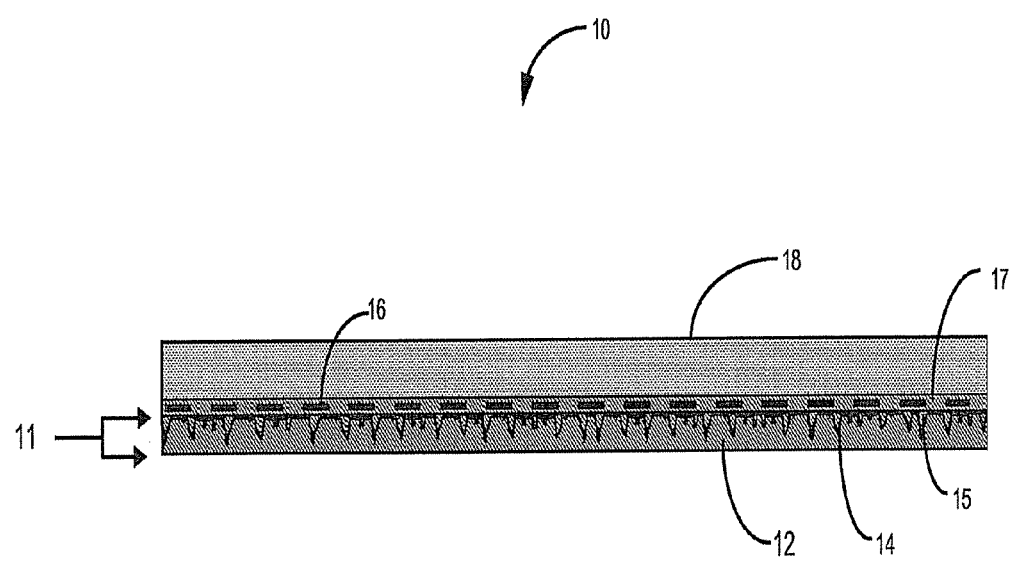
FIG. 1a is a cross-sectional view of an electrolytic capacitor.
FIG. 1b is a cross-sectional view of an implantable cardioverter-defibrillator including an electrolyte capacitor.

The following description of the preferred embodiment is merely exemplary in nature and is in no way intended to limit the invention, its application, or uses. For purposes of clarity, similar reference numbers are used in the drawings to identify similar elements.

One embodiment of the present invention is directed to an electrolytic capacitor that exhibits an operating voltage of 90% or more of the formation voltage. Operating voltage is the maximum voltage to which a capacitor is charged. Formation voltage is a voltage maintained during a process in which an oxide layer, an insulator, is grown on a surface of the anode. Operationally, formation voltage is the voltage above which the anode begins to draw significantly higher current as substantial amounts of oxide are grown across the surface of the anode to support the higher voltages. Formation voltage and formation temperature follow the relationship $T_f V_f$=constant, where $T_f$ is the formation temperature and $V_f$ is the formation voltage. [A F Torrisi, "Relation of Color to Certain Charatcteristics of Anodic Tantalum Films," Journal of the Electrochemical Society, Vol 102, No 4, pp 176-180, April 1955.] For oxides formed at different temperatures, the formation voltage should be corrected to the application temperature for appropriate comparison to the operating voltage.

In another embodiment, operating voltage of 90% or more of the formation voltage is based upon the electrolyte of the electrolytic capacitor. More specifically, the present invention's rated voltage is about 98% of the formation voltage. An exemplary electrolyte includes ingredients comprising acetic acid, ammonium acetate, phosphoric acid, tetraethylene glycol dimethyl ether, and water.

Another aspect of the present invention relates to designing an electrolytic capacitor capable of achieving an operating voltage of 90% or more of the formation voltage. There are several design considerations. For example, one consideration is dielectric breakdown of an electrolytic capacitor. Another exemplary consideration is equivalent series resistance (ESR) related to movement of charge between the anode and the cathode of the electrolytic capacitor. Skilled artisans will appreciate that the present invention achieves 15-18% improvement in energy density for the electrolytic capacitor.

FIG. 1a is a cross-sectional view of an electrolytic capacitor 10. Electrolytic capacitor 10 includes an anode 11, a cathode 18, a separator 16 therebetween, and an electrolyte 17. Anode 11 includes a metal layer 12 and an oxide layer 15.

Metal layer 12 is an anodic material such as tantalum (Ta), or other suitable material. Oxide layer 15 forms in pores 14 on metal layer 12. Formation of oxide layer 15 occurs when metal layer 12, exposed to a different electrolyte in a bath, has high voltage (e.g. up to 390 volts (V)) applied between metal layer 12, which is the positive terminal and a negative terminal (not shown). FIG. 1b is a cross-sectional view of an implantable cardioverter-defibrillator 1 including the electrolytic capacitor 10.

One embodiment of the invention relates to an electrolyte that includes glacial acetic acid ($HC_2H_3O_2$), ammonium acetate ($NH_4(C_2H_3O_2)$), phosphoric acid ($H_3PO_4$), water, and tetraethylene glycol dimethyl ether ($CH_2(OCH_2CH_2)_4OCH_3$). Exemplary quantities for the electrolyte ingredients are presented in Tables I and II below. These electrolyte 17 formulations were evaluated after being introduced to a set of 0.095 inch thick anode slug in electrolytic capacitors. Electrolyte 17 formulations were selected based on differing conductivities and/or breakdown voltages.

As shown in Table I, each electrolyte formula included a variety of different molarities for each ingredient. For example, tetraethylene glycol dimethyl ether ranged from about 0.9 molarity for electrolyte 1 to about 1.43 molarity for electrolyte 4. Water is the remaining portion.

TABLE I

Molarities of ingredients to form the electrolyte

| Exemplary quantities of ingredients for electrolyte | Glacial acetic acid | Ammonium Acetate | Phosphoric acid | Tetraethylene glycol dimethyl ether |
|---|---|---|---|---|
| 1 | 2.5 | 2.0 | 0.03 | 0.9 |
| 2 | 2.1 | 1.65 | 0.04 | 1.25 |
| 3 | 1.7 | 1.3 | 0.05 | 1.6 |
| 4 | 1.9 | 1.48 | 0.045 | 1.43 |
| 5 | 2.02 | 1.58 | 0.042 | 1.32 |

TABLE II

Mass (grams) per 2-liters of solution

| Electrolyte | Glacial acetic acid | Ammonium Acetate | Phosphoric acid | Tetraethylene glycol dimethyl ether | Water |
|---|---|---|---|---|---|
| 6 | 300 | 308 | 6 | 400 | 1060 |
| 7 | 252 | 254 | 9 | 556 | 1010 |
| 8 | 243 | 244 | 10 | 587 | 998 |

In one embodiment, the best electrolyte formulations depend on the desired operating voltage of capacitor 10. For example, electrolyte 8 in Table II is the best electrolyte 17 formula for an operating voltage of 255V.

Figure 2:
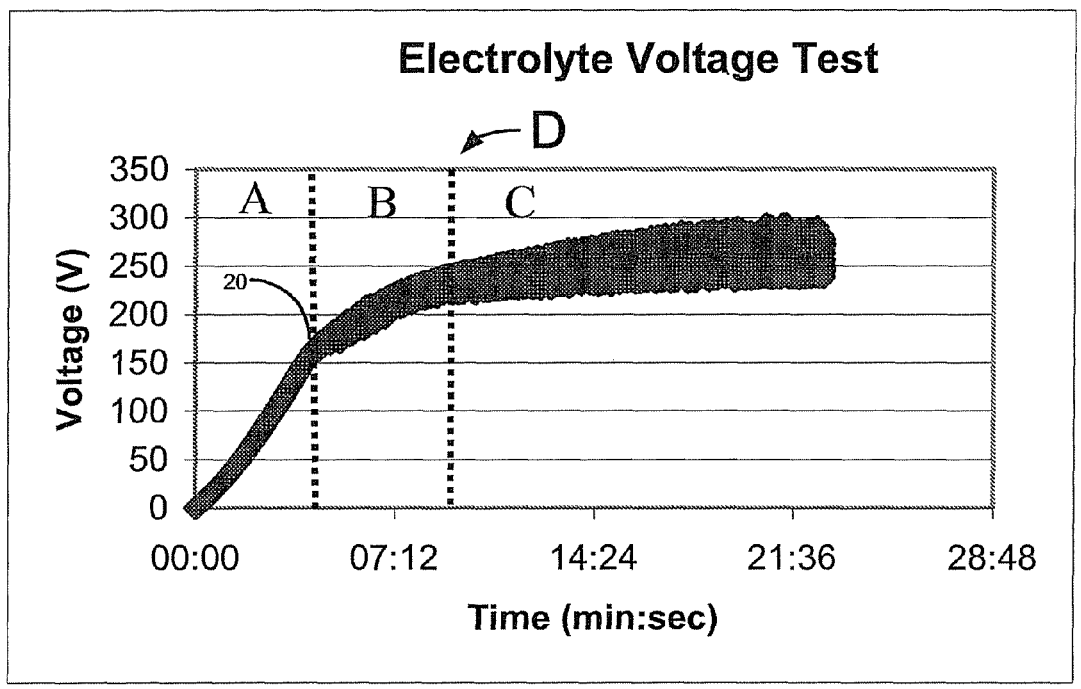
FIG. 2 is a graph that depicts exemplary electrolyte voltage regions.

Turning now to FIG. 2, a voltage curve from an electrolyte voltage test is shown which allows a designer of capacitor 10 to visually assess the performance of electrolyte 17 across a range of voltages. In this test, a constant current is applied to a tantalum wire in a sample of electrolyte. The voltage is monitored as a function of time. The observed voltage typically rises linearly for some time, then rises somewhat more slowly with increasing noise as parasitic processes absorb more of the applied current.

The voltage of the anode immersed in electrolyte 17 has an initial linear rise (Region A), a transition region (Region B) and a relatively flat, noisy region characterized by continuous steady-state breakdown and repair (Region C). Electrolytic capacitor 10 is least likely to degrade over time while operating in the linear region (Region A). The highest voltage in this region is a nominal working voltage 20 or nominal electrolyte voltage. Upon increasing voltage into the transition region (Region B), a trade-off occurs between the efficiencies of a higher operating voltage and charge time stability of capacitor 10. In the transition region, charge time begins to show some instability due to greater oxide susceptibility to reaction with electrolyte 17. Beyond the transition region, actual breakdown occurs of oxide layer 15.

Numerous factors may be contemplated to design capacitor 10. In one embodiment, capacitor 10 is designed by consideration of the working voltage and the nominal working voltage. Nominal working voltage measures the ability of electrolyte 17 to withstand voltage whereas working voltage is the capacitor-level assessment of the highest voltage at which electrolyte 17 may be used. In one embodiment, a designer of capacitor 10 may set working voltage above the nominal working voltage at a value that balances competing design goals. To illustrate, by setting working voltage at a level above the nominal working voltage, battery size of an implantable medical device (IMD) may increase due to increased charge time and leakage losses but ESR-type heating losses may be reduced. Reduction of ESR is due to a more conductive electrolyte 17, which also reduces the size of capacitor 10. Other design considerations may include the lifetime of capacitor 10, operating temperature of capacitor 10, charge time of capacitor 10, battery life, overall IMD size, and operating voltage of capacitor 10. Electrolyte 17 can be used 50 volts (V) higher than the nominal electrolyte voltage. Additionally, electrolyte 17 achieved an operating voltage that is above 90% of anode slug formation voltage. In one embodiment, capacitor 10 has an operating voltage that is above 93% of anode slug formation voltage. In another embodiment, capacitor 10 has an operating voltage that is above 95% of anode slug formation voltage. In still yet another embodiment, capacitor 10 has an operating voltage that is above 98% of anode slug formation voltage.

Operating at a higher fraction of formation voltage increases energy density, since $E=(½) CV^2$, where E is energy, C is capacitance, and V is operating voltage of capacitor 10. Capacitance is defined as $C=(KA)/d$ where K is the dielectric constant, A is the surface area of oxide layer 15, and d is the thickness of oxide layer 15.

Capacitance decreases and operating voltage increases when oxide layer 15 is formed to a higher voltage (and consequently to a greater thickness). The increase in energy density from these factors may outweigh possible limitations associated with lower conductivity (higher required porosity, lower powder density, thinner anodes, and/or reduced high frequency performance, etc.), increased leakage current, or charge time. Increased energy density, which depends on the increased operating voltage, reduces the size of the ICD.

In order to further enhance the performance of electrolyte 17, additives may be added to the mixture of electrolyte 17 ingredients listed in Tables I and II. Organic solvents or salts (e.g. ammonium azelate, potassium phosphate etc.) may be used to adjust (increase or decrease) the nominal working voltage while reducing the conductivity associated with electrolyte 17. For electrolyte not at a pH 7.0, increased conductivity may be achieved by addition of hydronium ions, hydroxide ions, or other suitable additive(s).

In another embodiment, improving characteristics associated with oxide layer 15 may also improve the operating voltage. Oxide susceptibility to leakage and breakdown may be significantly reduced, allowing operation to occur beyond the nominal working voltage. The selection of ingredients for electrolyte 17 may synergistically enhance capacitor 10 (e.g. the higher voltage capacitor, a desirable therapy voltage with a three-capacitor system, higher energy density capacitor etc.) in combination with suitably processed capacitor oxides.

Oxide properties and thickness are affected by oxide formation conditions. Exemplary oxide formation conditions include temperature of metal layer 12 in an electrolytic environment (e.g. electrolyte bath etc.), hold time at final formation voltage, and the final electrical current density through metal layer 12 at termination of the formation process.

Experimental data from two separate experiments confirmed that electrolyte 17 achieves an operating voltage of 90% or more of the formation voltage. The two experiments also explored the manner in which competing design goals were affected. As a preliminary manner, electrolytes 1 through 8 in Tables I and II were formulated to provide nominal electrolyte voltages between 175 V and 225 V for both experiments.

Figure 3:
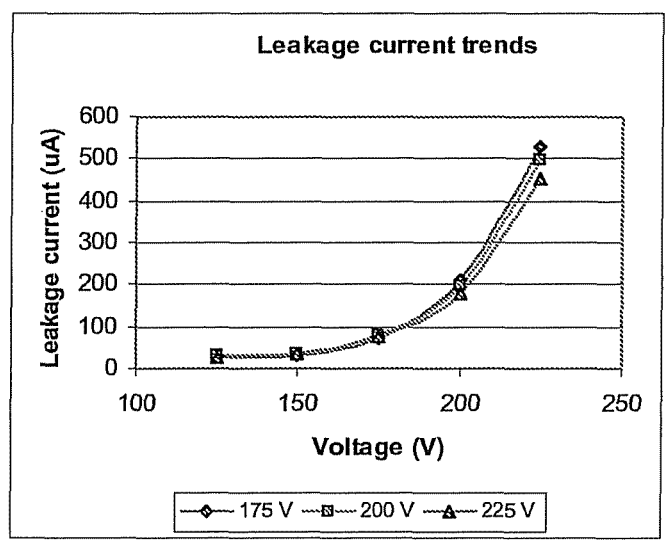
FIG. 3 is a graph that depicts leakage current trends versus voltage.
Figure 4:
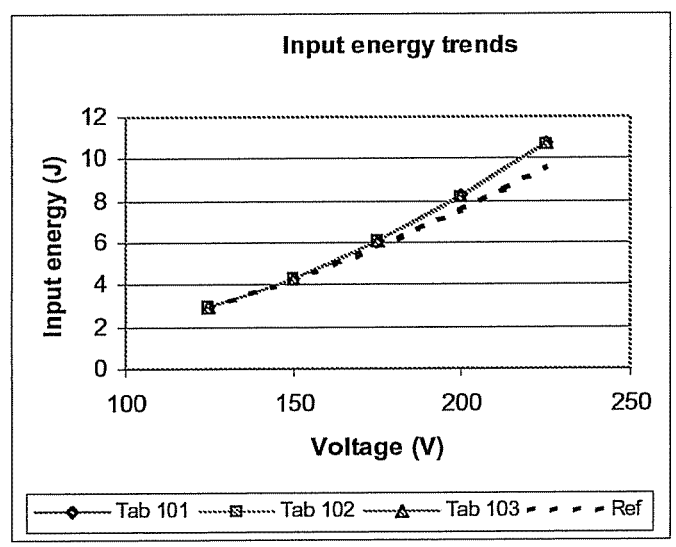
FIG. 4 is a graph that depicts energy input versus voltage.
Figure 5:
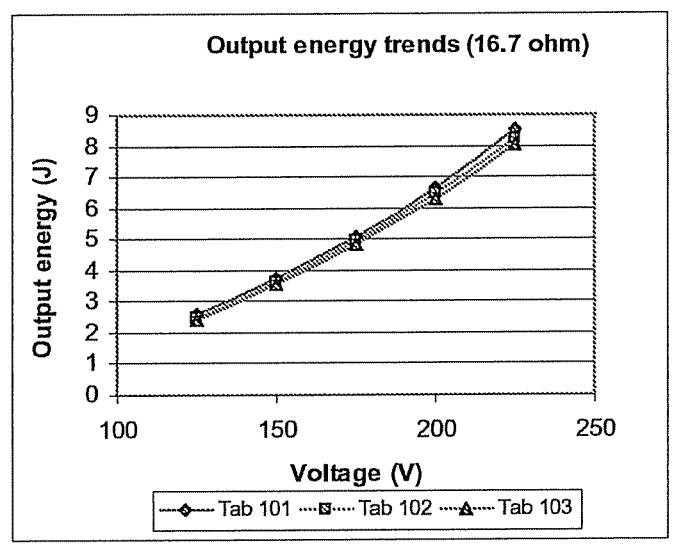
FIG. 5 is a graph that depicts output energy trends versus voltage.

FIGS. 3-5 relate to the first experiment whereas FIGS. 7-12 relate to the second experiment. Several general observations were made based upon the experiments. For example, capacitor 10 does not become abruptly nonfunctional at a higher voltage. Electrolyte 17 is usable for somewhat higher voltages, with some possibility of increasing charge times over many charging cycles. The primary trade-off is between leakage current and ESR. These properties may change over the life of capacitor 10.

Increasing conductivity of electrolyte 17 increases the accessibility of charge stored in the interior of the anode slug. Electrolyte 17 should be sufficiently conductive to allow access to charge in the interior of the anode slug on the timescale of the application charge/discharge cycle.

Referring to Table 3, nine capacitors were examined to determine the effects of a particular electrolyte 17 formula from Table I.

All capacitors 10 were constructed from slugs prepared under the same formation conditions and formed to 225 V. Conservative working voltages were used for formulations of electrolyte 17. Typical formation conditions and/or processes are disclosed in U.S. Pat. No. 5,716,511 entitled "Anodizing electrolyte and its use and U.S. Pat. No. 6,480,371 entitled, "Alkanolamine-phosphoric acid anodizing electrolyte" both of which are incorporated by reference in relevant parts. Low leakage current powders with CV in the range of 10,000 to 20,000 microfarad*volt/gram (uF V/g) are appropriate for this testing, where CV represents a standard rating of a capacitor powder, the expected capacitance multiplied by the voltage. Suitable powders are available from H C Starck Incorporated or Cabot Corporation.

All exemplary electrolytes 17 show a clear progression in capacitance and ESR. As the electrolyte resistivity increases, average ESR progresses from 1.1Ω to 1.5Ω to 2.0Ω, nearly doubling as resistivity is doubled. Additionally, capacitance drops from 344 μF to 335 μF to 328 μF, reflecting the reduced electrical access to the slug interior at 120 Hz, which represents the relevant time scale of ICD function.

FIG. 3 compares average leakage currents for the three electrolytes of Table III. On FIG. 3, traces are labeled relative to the nominal electrolyte voltage of capacitor 10. Leakage current rises rapidly upon approaching the formation voltage. The lower nominal voltage electrolyte may exhibit higher leakage current; however, the small sample size lacks sufficient statistical data. A tradeoff between leakage current and ESR/capacitance may exist. Leakage currents are measured after five minutes at a particular voltage, according to standard practices. Results are averaged over the available parts. Capacitance, ESR and leakage current all contribute to energy density. Energy density is a significant consideration for an ICD. The present invention achieves 15-18% improvement in energy density for the electrolytic capacitor.

FIG. 4 shows the variations in input energy with charge voltage of electrolyte 17. The dashed line is a projection of the 125 V energy to higher voltages, assuming an ideal scale with $V^2$. of $E=(\frac{1}{2}) CV^2$ For capacitor 10, about a joule of additional energy is required at 225 V due to energy losses. Electrolytes 1-3 are tabs 101,102, and 103, respectively.

FIG. 5 represents the output energy trends for capacitor 10 discharged into a 16.7Ω load, which generally correlates to a nominal 50Ω patient load for a three capacitor system in an IMD. These output energies are measured on discharging to 0 volts. The lower nominal voltage, higher conductivity electrolytes have consistently higher output energies. At 225 V,

TABLE III

Capacitor inventory

| Electrolyte Example | Nominal Electrolyte Voltage (Volts) | Electrolyte Resistivity Ohm Centimeters (Ω cm) | Anode Number | Serial Number | Capacitance microFarad (μF) | ESR (ohm (Ω)) |
|---|---|---|---|---|---|---|
| 1 | 175 | 23.3 | 4 | 35 | 344.0 | 1.081 |
| 2 | 200 | 34.7 | 2 | 38 | 335.9 | 1.469 |
| 2 | 200 | 34.7 | 5 | 23 | 329.2 | 1.529 |
| 2 | 200 | 34.7 | 8 | 5 | 338.6 | 1.412 |
| 3 | 225 | 42.0 | 3 | 6 | 327.4 | 2.024 |
| 3 | 225 | 42.0 | 6 | 21 | 329.9 | 2.061 |
| 3 | 225 | 42.0 | 7 | 46 | 325.5 | 2.041 | there is a 0.5 joules (J) difference between the electrolyte 1 and electrolyte 3. Within this data set, electrolyte 1 for capacitor 10 delivers the most energy. It was also observed that ESR losses outweigh leakage current effects.

Figure 6:
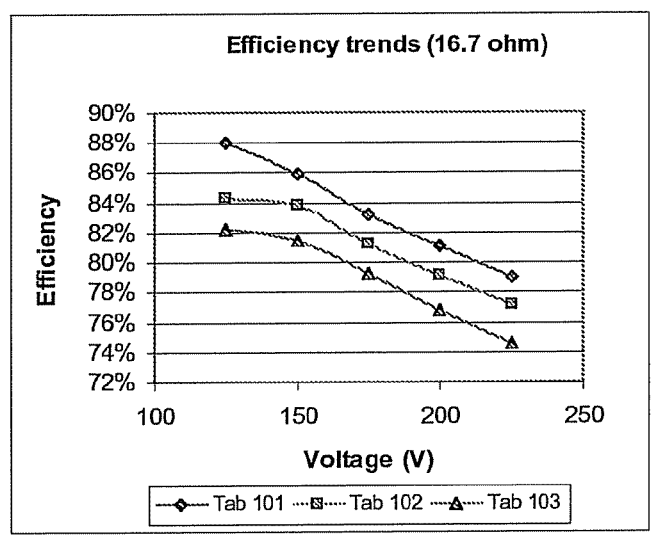
FIG. 6 is a graph that depicts efficiency trends versus voltage.

FIG. 6 depicts the general downward slope in efficiency primarily related to charging losses. The gap between the curves is primarily related to ESR differences.

Figure 7:
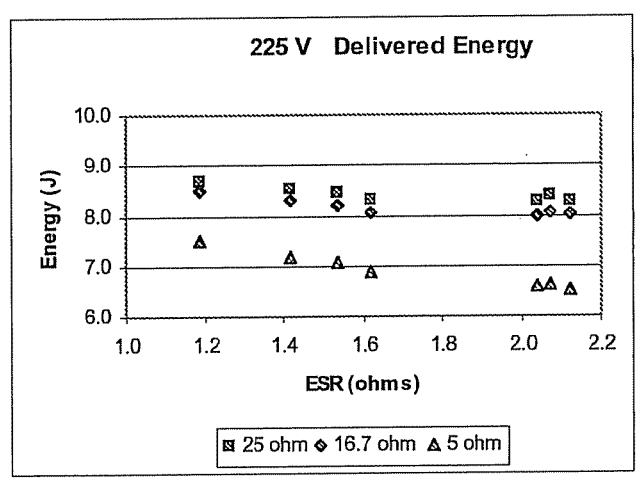
FIG. 7 is a graph that depicts delivered energy versus equivalent series resistance (ESR)

FIG. 7 depicts delivered energy for each of capacitors 10 charged to 225 V as a function of ESR. As shown, data below 1.3Ω represents electrolyte 1; between 1.3Ω and 1.8Ω represents electrolyte 2; and electrolyte 3 capacitors appear above 1.8Ω. As expected, there is a reduction in delivered as the internal resistance of capacitor 10 increases, and the reduction is more pronounced with smaller loads. This effect is due to the ESR (measured at 120 Hz) acting as a voltage divider in series with the load resistance.

From the first experiment, a number of observations were made. For example, electrolyte 17 is effectively used at 50 V above its nominal breakdown voltages. Moreover, leakage current losses do not compete with ESR losses. Additionally, conductivity outweighs leakage current in choosing an electrolyte formulation. The impact of slower ionic access to the interior of the slug was assessed to be less than 2% of delivered energy efficiency.

For the second experiment, capacitors 10 were used to examine the dependence of delivered energy and charge/discharge efficiency on electrolyte conductivity. Capacitors were made of two types of anode powder, Type 1 and Type 2. Four different electrolytes of increasing conductivity and decreasing nominal working voltage were used.

Capacitors were tested at various voltages, as shown on Table IV.

TABLE IV

Test voltages for capacitors by electrolyte

| Anode Powder Type | $1^{st}$ test voltage | $2^{nd}$ test voltage | $3^{rd}$ test voltage | $4^{th}$ test voltage | $5^{th}$ test voltage |
|---|---|---|---|---|---|
| Type 1 | 150 | 175 | 200 | 220 | |
| Type 2 | 150 | 175 | 200 | 220 | 260 |

At each voltage, a series of tests were performed including 5 minute leakage current test, ESR, and capacitance, charge energy, charge time, and discharge energy. For the first two voltages, 25Ω, 16.7Ω, and 5Ω loads were used. For other testing, only 16.7-Ω nominal loads were used, corresponding to a 50-Ω load for a 3-capacitor system. Discharge energies were determined for full discharge and for discharge to 25% of charge voltage. Tests were performed at 37 degree Celsius (° C.).

Figure 8:
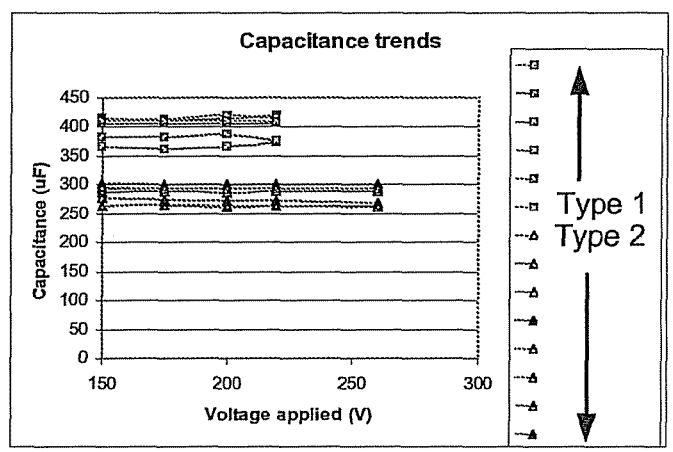
FIG. 8 is a graph that depicts capacitance versus voltage.

Capacitance is displayed in FIG. 8. Capacitor 10 made with either Type 1 or Type 2 powder but with the same electrolyte 17 have similar ESR. The Type 2 capacitors are lower capacitance, but their ability to be charged to a higher voltage provides a similar total available energy.

Figure 9:
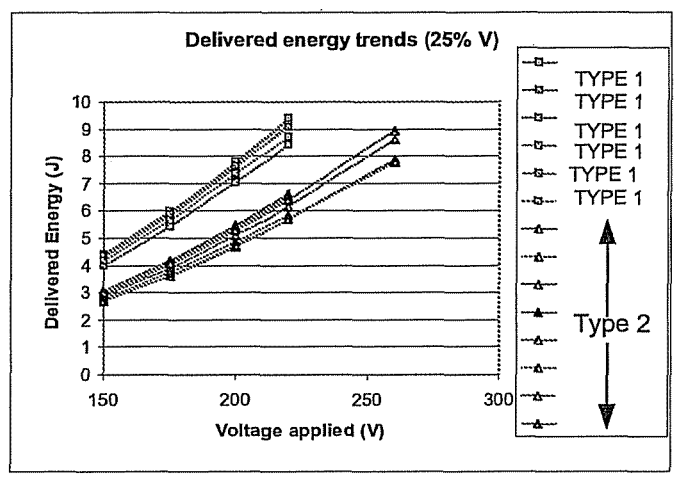
FIG. 9 is a graph that depicts delivered energy trends versus applied voltage.
Figure 10:
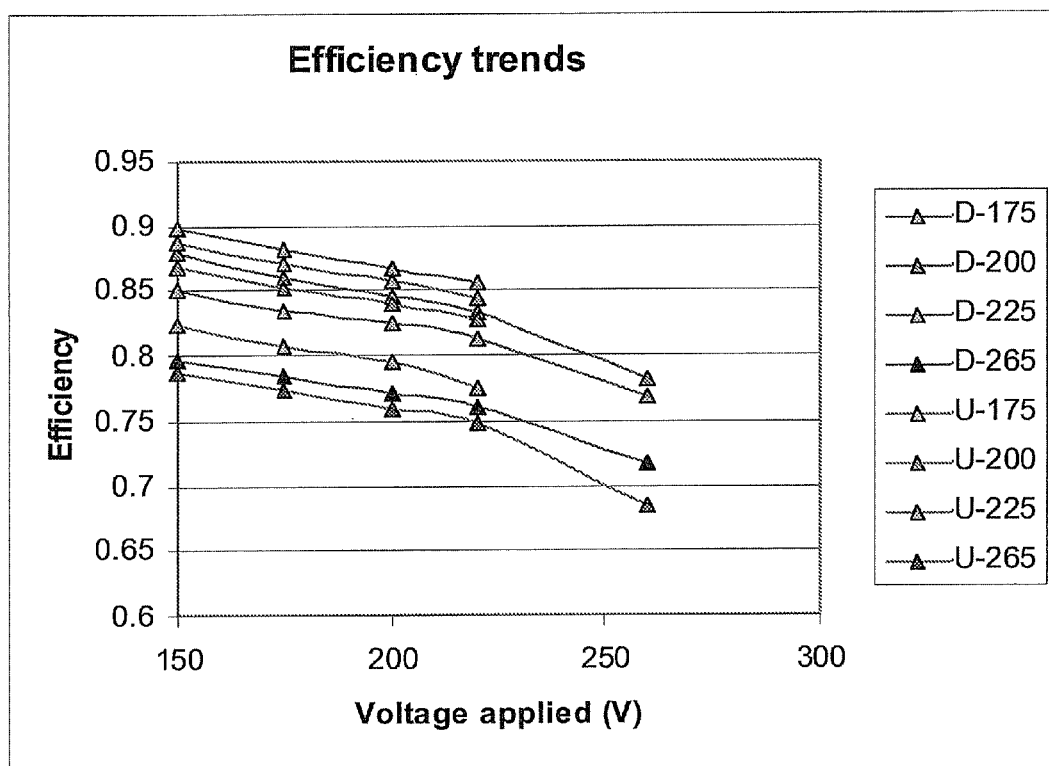
FIG. 10 is a graph that depicts efficiency trends versus applied voltage.

FIG. 9 relates delivered energy for discharge into a 16.7 ohm load to 25% of voltage for capacitors made with Type 2 powders. Input and discharge energies are combined in FIG. 10 as overall efficiency, defined as discharge energy divided by input energy. The figure indicates two runs ("D" and "U") with indicated electrolyte voltages. Full discharge efficiency starts at about 90% for Type 2 powder capacitors charged to 150 V. It falls off with applied voltage and higher nominal electrolyte voltage.

Figure 11:
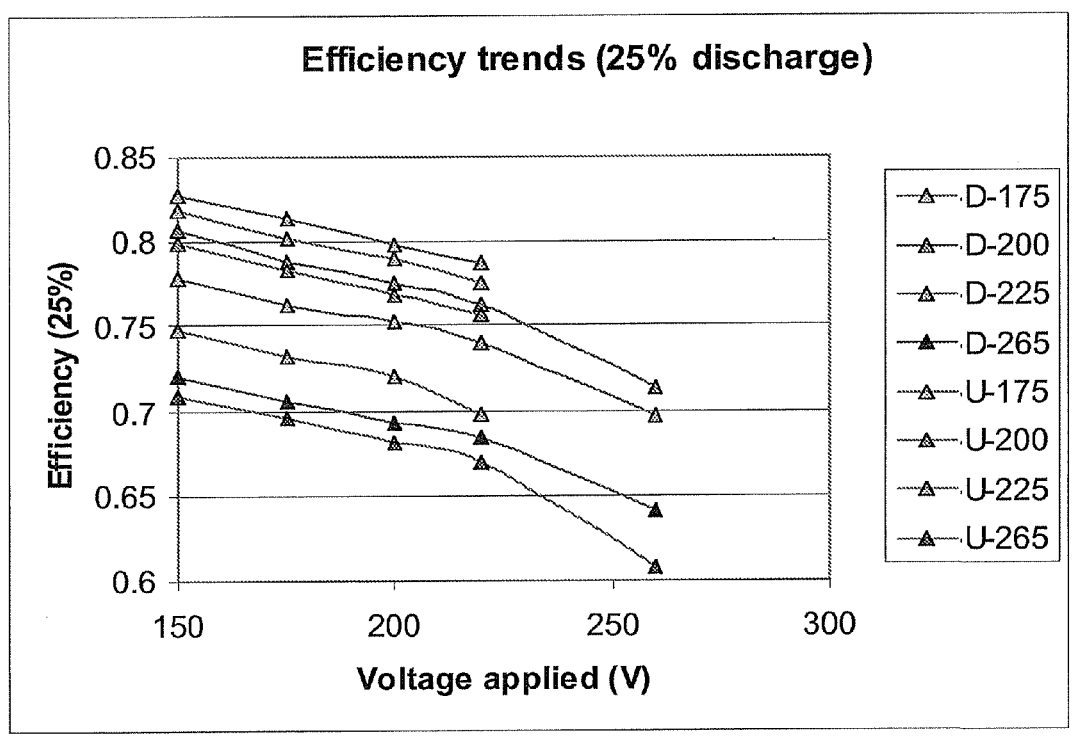
FIG. 11 is a graph that depicts efficiency trends versus applied voltage for discharge to 25% of the voltage.

Similar trends are seen in FIG. 11 for discharge to 25% of applied voltage. This figure also indicates two runs ("D" and "U") with indicated electrolyte voltages. Initial efficiencies are slightly lower, in part due to 1/16 of the energy remaining on the capacitors; ideal efficiency would be only 94%. Inefficiencies increase as applied voltage and electrolyte resistivity are increased.

Figure 12:
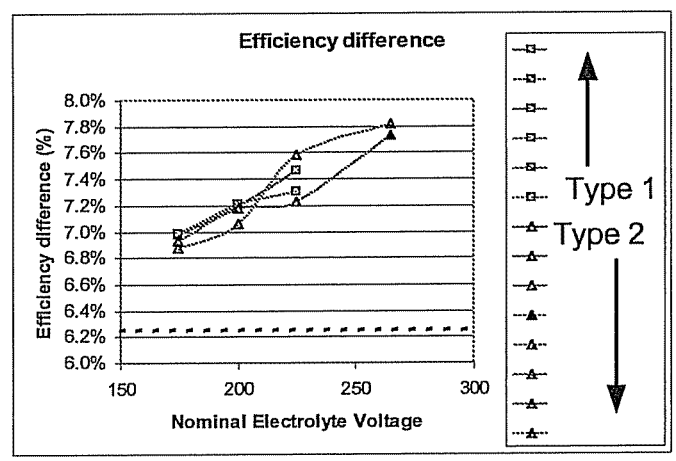
FIG. 12 is a graph that depicts efficiency trends versus voltage.

FIG. 12 shows the marginal efficiency loss of operating at 25% discharge instead of at full discharge of capacitor 10. This representative data is taken at 150 V. The dotted line indicates the efficiency loss expected from the energy remaining on the capacitor. The loss above this threshold is related to losses due to slow access to the slug interior compared to the time scale of the discharge. These losses are less than 2% for this set of capacitors.

An implantable cardioverter-defibrillator (ICD) application involves capacitor operation at a very stable temperature (e.g. about 37° C.) with a small number of cycles (e.g. less than 200) and a very short time (e.g. less than 15 minutes) at a certain voltage over the capacitor 10 lifetime. These conditions, prevent a higher level of parasitic activity from significantly impacting the capacitor lifetime. Additionally, the electrolyte allows creation of a higher energy density capacitor which in turn allows for production of a smaller implantable medical device (IMD).

Figure 13:
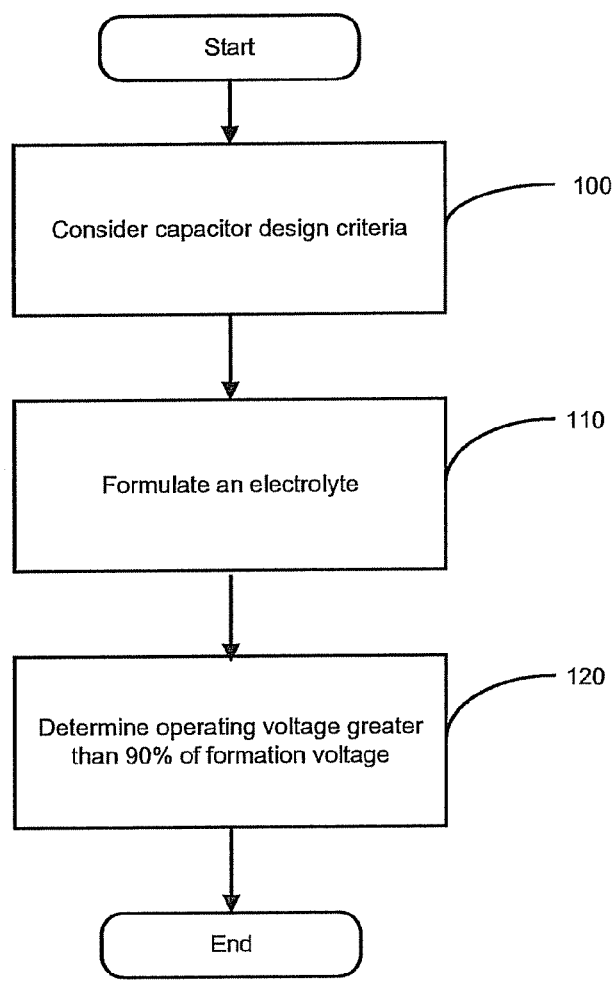
FIG. 13 is a flow diagram for producing a capacitor capable of an operating voltage that is 90% or more of its formation voltage.

FIG. 13 is a flow diagram for designing an electrolytic capacitor. At block 100, at least one capacitor design criteria is considered. The design criteria includes voltage breakdown, ESR, conductivity of an electrolyte associated with the electrolytic capacitor, and leakage current. At block 110, operating voltage is determined relative to formation voltage. At block 120, an electrolyte is formulated such that an operating voltage is greater than 90 percent of a formation voltage for a capacitor.

Skilled artisans will appreciate that alternative embodiments may be formed by implementation of the claimed invention. For example, electrolyte 17 ingredients are selected for certain design conditions but different ingredients and/or quantities may be appropriate for different designs. Additionally, adjustment of nominal working voltage may generally be performed around any desired capacitor operating or surge voltage.

The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A method of using an implantable cardioverter-defibrillator, the method comprising:
   providing an implantable cardioverter-defibrillator comprising an electrolytic capacitor comprising:
      an anode comprising tantalum;
      a cathode;
      a separator coupled to the anode and the cathode;
      an electrolyte comprising water over the anode, cathode, and separator; and
      an oxide layer on the anode that is formed at a formation voltage; and
   charging the capacitor repeatedly to an operating voltage of greater than 90 percent of its formation voltage during use of the cardioverter-defibrillator.

2. The method of claim 1, wherein the electrolyte further includes ingredients comprising acetic acid, ammonium acetate, phosphoric acid, and tetraethylene glycol dimethyl ether.

3. The method of claim 2, wherein the acetic acid includes a molarity which ranges from about 1.5 to about 2.5.

4. The method of claim 2, wherein the ammonium acetate includes a molarity which ranges from about 1.2 to about 2.1.

5. The method of claim 2, wherein the phosphoric acid includes a molarity which ranges from about 0.02 to about 0.5.

6. The method of claim 2, wherein the tetraethylene glycol dimethyl ether includes a molarity which ranges from about 0.8 to about 1.5.

7. The method of claim 1, wherein the electrolyte has a working voltage at least equivalent to its nominal working voltage.

8. The method of claim 1, wherein the electrolyte has a working voltage greater than its nominal working voltage.

9. The method of claim 1, wherein charging the capacitor comprises charging the capacitor repeatedly to an operating voltage of greater than 93 percent of its formation voltage during use of the cardioverter-defibrillator.

10. The method of claim 9, wherein charging the capacitor comprises charging the capacitor repeatedly to an operating voltage of greater than 95 percent of its formation voltage during use of the cardioverter-defibrillator.

11. The method of claim 10, wherein charging the capacitor comprises charging the capacitor repeatedly to an operating voltage of greater than 98 percent of its formation voltage during use of the cardioverter-defibrillator.

12. The method of claim 1, wherein charging the capacitor comprises charging the capacitor repeatedly to an operating voltage of greater than 90 percent of its formation voltage during use of the cardioverter-defibrillator.

13. A method of using an implantable cardioverter-defibrillator, the method comprising:
   providing an implantable cardioverter-defibrillator comprising an electrolytic capacitor prepared by a method comprising:
     selecting an anode comprising tantalum;
     coupling a cathode and a separator to the anode;
     formulating an electrolyte comprising water;
     placing the electrolyte over the anode, cathode, and separator; and
     forming an oxide layer on the anode at a formation voltage;
     wherein, the capacitor is constructed of materials and under conditions such that the capacitor has an operating voltage greater than 90 percent of its formation voltage, and
   charging the capacitor repeatedly to an operating voltage of greater than 90 percent of its formation voltage during use of the cardioverter-defibrillator.

14. The method of claim 13, wherein formulating an electrolyte comprises selecting ingredients comprising water, acetic acid, ammonium acetate, phosphoric acid, and tetraethylene glycol dimethyl ether.

15. The method of claim 14, wherein the acetic acid includes a molarity which ranges from about 1.5 to about 2.5.

16. The method of claim 14, wherein the ammonium acetate includes a molarity which ranges from about 1.2 to about 2.1.

17. The method of claim 14, wherein the phosphoric acid includes a molarity which ranges from about 0.02 to about 0.5.

18. The method of claim 14, wherein the tetraethylene glycol dimethyl ether includes a molarity which ranges from about 0.8 to about 1.5.

19. The method of claim 13, wherein formulating the electrolyte comprises formulating the electrolyte to have a working voltage at least equivalent to its nominal working voltage.

20. The method of claim 13, wherein formulating the electrolyte comprises formulating the electrolyte to have a working voltage greater than its nominal working voltage.

21. The method of claim 13, wherein charging the capacitor comprises charging the capacitor repeatedly to an operating voltage of greater than 90 percent of its formation voltage during use of the cardioverter-defibrillator.

22. An implantable cardioverter-defibrillator comprising an electrolytic capacitor comprising:
   an anode comprising tantalum;
   a cathode;
   a separator coupled to the anode and the cathode;
   an electrolyte comprising water, acetic acid, ammonium acetate, phosphoric acid, and tetraethylene glycol dimethyl ether; and
   an oxide layer on the anode that is formed at a formation voltage.

23. A method of using an implantable cardioverter-defibrillator, the method comprising:
   providing an implantable cardioverter-defibrillator comprising an electrolytic capacitor comprising:
     an anode comprising tantalum;
     a cathode;
     a separator coupled to the anode and the cathode;
     an electrolyte comprising water, acetic acid, ammonium acetate, phosphoric acid, and tetraethylene glycol dimethyl ether; and
     an oxide layer on the anode that is formed at a formation voltage; and
   charging the capacitor repeatedly to an operating voltage of greater than 90 percent of its formation voltage during use of the cardioverter-defibrillator.

24. An implantable cardioverter-defibrillator comprising an electrolytic capacitor comprising:
   an anode comprising tantalum;
   a cathode;
   a separator coupled to the anode and the cathode;
   an electrolyte comprising:
     water,
     about 1.5 to about 2.5 Molar acetic acid,
     about 1.2 to about 2.1 Molar ammonium acetate,
     about 0.02 to about 0.5 Molar phosphoric acid, and
     about 0.8 to about 1.5 Molar tetraethylene glycol dimethyl ether; and
   an oxide layer on the anode that is formed at a formation voltage.

25. A method of using an implantable cardioverter-defibrillator, the method comprising:
   providing an implantable cardioverter-defibrillator comprising an electrolytic capacitor comprising:
     an anode comprising tantalum;
     a cathode;
     a separator coupled to the anode and the cathode;
     an electrolyte comprising:
       water,
       about 1.5 to about 2.5 Molar acetic acid,
       about 1.2 to about 2.1 Molar ammonium acetate,
       about 0.02 to about 0.5 Molar phosphoric acid, and
       about 0.8 to about 1.5 Molar tetraethylene glycol dimethyl ether; and
     an oxide layer on the anode that is formed at a formation voltage; and charging the capacitor repeatedly to an operating voltage of greater than 90 percent of its formation voltage during use of the cardioverter-defibrillator.

* * * * *

UNITED STATES PATENT AND TRADEMARK OFFICE
CERTIFICATE OF CORRECTION

PATENT NO. : 8,675,348 B2  
APPLICATION NO. : 12/843853  
DATED : March 18, 2014  
INVENTOR(S) : Mark E. Viste et al.

Page 1 of 1

It is certified that error appears in the above-identified patent and that said Letters Patent is hereby corrected as shown below:

On the Title Page, Item (60)

Under Related U.S. Application Data:

Delete:

"Division of application No. 11/427,919, filed on Jun. 30, 2006, now Pat. No. 7,952,853, which is a continuation-in-part of application No. 10/832,766, filed on Apr. 27, 2004, now Pat No. 7,081,141, and a continuation-in-part of application No. 10/977,584, filed on Oct. 29, 2004, now abandoned."

and insert:

-- Division of application No. 11/427,919, filed on Jun. 30, 2006, now Pat. No. 7,952,853. --

Signed and Sealed this
Tenth Day of March, 2015

Michelle K. Lee
*Deputy Director of the United States Patent and Trademark Office*